United States Patent
Meisner

(12) 
(10) Patent No.: US 6,217,914 B1
(45) Date of Patent: Apr. 17, 2001

(54) ASCORBIC ACID COMPOSITION AND METHOD FOR TREATMENT OF AGING OR DAMAGED SKIN

(75) Inventor: Lorraine Faxon Meisner, Madison, WI (US)

(73) Assignee: Bioderm, Inc., Madison, WI (US)

( * ) Notice: Subject to any disclaimer, the term of this patent is extended or adjusted under 35 U.S.C. 154(b) by 0 days.

(21) Appl. No.: 09/356,142

(22) Filed: Jul. 19, 1999

Related U.S. Application Data

(60) Provisional application No. 60/125,356, filed on Mar. 19, 1999.

(51) Int. Cl.[7] .................. A61K 31/19; A61K 31/21; A61K 31/34; A61K 31/66

(52) U.S. Cl. .................. 424/642; 514/23; 514/25; 514/62; 514/75; 514/474; 514/494; 514/506; 514/532; 514/534; 514/538; 514/546; 514/551; 514/557; 514/561; 514/562; 514/563; 514/564; 514/567; 514/568; 514/574; 514/576; 514/579; 514/646; 514/663; 514/665; 514/666; 514/667; 514/673; 514/674; 514/706; 514/707; 514/712; 514/724; 514/727; 514/728; 514/729; 514/730; 514/731; 514/738; 514/740; 514/741; 514/772; 514/777; 514/781; 514/886; 514/887; 424/641; 424/709

(58) Field of Search .................. 424/641, 642, 424/709; 514/474, 494, 567, 532, 546, 551, 561, 562, 563, 62, 886, 887, 23, 25, 75, 506, 534, 538, 557, 564, 568, 574, 576, 579, 646, 663, 665, 666, 667, 673, 674, 706, 707, 712, 724, 727, 728, 729, 730, 731, 738, 740, 741, 772, 777, 781

(56) References Cited

U.S. PATENT DOCUMENTS

| | | | |
|---|---|---|---|
| 2,400,171 | 5/1946 | Ruskin et al. | 514/474 |
| 2,442,461 | 6/1948 | Karrer | 514/474 |
| 2,585,580 | 2/1952 | Oppit | 514/474 |
| 3,886,265 | 5/1975 | Evers et al. | 424/49 |
| 4,229,430 | 10/1980 | Fahim et al. | 424/49 |
| 4,294,852 | 10/1981 | Wildnauer et al. | 424/317 |
| 4,367,157 | 1/1983 | Sherman | 252/106 |
| 4,515,771 | 5/1985 | Fine | 424/52 |
| 4,590,067 | 5/1986 | Meisner | 424/54 |
| 4,647,453 | 3/1987 | Meisner | 424/54 |
| 4,711,780 | 12/1987 | Fahim | 424/145 |
| 4,722,936 | 2/1988 | Jacob | 514/474 |
| 4,772,591 | 9/1988 | Meisner | 514/62 |
| 4,818,521 | 4/1989 | Tamabuchi | 424/62 |
| 4,938,969 | 7/1990 | Schintsky et al. | 424/642 |
| 4,983,382 | 1/1991 | Wilmott et al. | 424/62 |
| 5,140,043 | 8/1992 | Darr et al. | 514/474 |
| 5,516,793 | 5/1996 | Duffy | 514/474 |
| 5,703,122 | 12/1997 | Duffy | 514/474 |
| 5,736,567 | 4/1998 | Cantin et al. | 514/474 |
| 5,750,123 | 5/1998 | Znaiden et al. | 424/401 |
| 5,804,594 | * 9/1998 | Murad | 514/474 |

FOREIGN PATENT DOCUMENTS

| | | |
|---|---|---|
| 0 273 202 B1 | 6/1995 | (EP) . |
| 61-078715 | 4/1986 | (JP) . |

OTHER PUBLICATIONS

Bandelin, et al, *J. Am. Pharmacol. Assoc.*, 44(4), p. 241–244 (1955).

Bauerfeind, "Ascorbic Acid: Chemistry, Metabolism, Uses", Seib, et al., *Advances in Chemistry*, pp. 417–429 (1982).

Bekesi, et al, *Cancer Research*, 29, 353–359 (1969).

Black, *Photochemistry and Photobiology*, 46: 213–221 (1987).

Borne, et al, *J. Med. Chem.*, 15(12), 1325–1326 (1972).

Cooke, et al., "Vitamin C (Ascorbic Acid)", from conference in Warwick, Coventry (Apr. 1981), pp. 167–168, 170–171, Published by Applied Science Publishers.

Englard, et al., *Ann.Rev.Nutri.*, 6:365–394 (1986).

Gualano, et al., *Pharmacology Res. Commun.*, 15(7) (Jul. 1983).

Hajratwala, *S.T.P. Pharma*, 1(4), 281–286 (1985).

Hall, et al., *J. Pharm.*, 69(12), 1451–1452 (1989).

Hornig, et al., "Vitamin C (Ascorbic Acid)", from conference in Warwick, Coventry (Apr. 1981), pp. 225–226, Published by Applied Science Publishers.

Imai, et al., *Jap. J. Pharmacol. Assoc.*, 317 (1967).

Jain, et al., *Agents and Actions*, 11(3), 243 (1981).

Kahn et al., *Arch. Dermatol.*, 109, 510–517 (1974).

Kaplan, et al., *J. Cutaneous Aging Cosmetic Derm.*, 1(2), 115–121 (1988/1989).

(List continued on next page.)

Primary Examiner—John Pak
Assistant Examiner—Frank Choi
(74) Attorney, Agent, or Firm—Foley & Lardner

(57) ABSTRACT

An ascorbic acid-based composition and related method for the treatment of aging or photo-damaged skin is disclosed. The composition includes water and ascorbic acid, at least a portion of which has generally been pretreated by being dissolved under relatively high temperature and concentration conditions. The composition typically includes at least about 5.0% (w/v) ascorbic acid and may advantageously be formulated to have a pH above 3.5. Generally, the composition also includes non-toxic zinc salt, tyrosine compound, and/or pharmaceutically acceptable carrier. In addition, the composition may include an anti-inflammatory compound, such as aminosugar and/or sulfur-containing anti-inflammatory compound. The topical composition may be in the form of a serum, a hydrophilic lotion, an ointment, a cream, or a gel.

35 Claims, 3 Drawing Sheets

OTHER PUBLICATIONS

Kassem et al., *Phamaceutica Acta Helvetiae*, 44, 611–623 (1969).
Kassem et al., *Pharma. Acta Helvetiae*, 47, 89–97 (1972).
Kolata, *Science*, 219, 377–378 (1983).
Kunert, et al., *Lipids*, 18, 271–273 (1983).
Kwapisziewski et al., *Arch. Immunol. Ther. Exp.*, 17(6), 729–731 (1979).
Laszlo, et al., *Journal of the National Cancer Institute*, 24, 267–278 (1960).
Lien, et al., *Formosan Med. Assoc.*, 75:243–250, (1976).
Litwin, *J. Cell Science*, 14, 671–678 (1974).
Nobile & Woodhill, "Vitamin C", p. 24, MIP Press Ltd., Boston, MA (1981).
Pinnell et al., Cutaneous Ageing, Eds. Kligman et al., Univ. of Tokyo Press, 275–292 (1988).
Smart et al., *Cancer Res.*, 47, 6633–6638 (1987).
Tapadinhas, et al., *Pharmatherapeutica*, 3(3), 157–168 (1982).
Thomas, et al., *J. Pharm. Pharmacol.*, 26(2), 151–152 (1974).
West, et al., *Textbook of Biochemistry*, p. 795, The MacMillan Company, New York (1951).

* cited by examiner

ASCORBIC ACID COMPOSITION AND METHOD FOR TREATMENT OF AGING OR DAMAGED SKIN

This application is a continuation-in-part of U.S. provisional application Ser. No. 60/125,356 (filed on Mar. 19, 1999), the disclosure of which is herein incorporated by reference.

BACKGROUND OF THE ART

Skin is composed of a top layer, the epidermis, which is approximately 20 cell layers or about 0.1 mm in thickness, and a lower layer, the dermis, which is from about 1 to about 4 mm in thickness and contains small blood vessels, collagen, elastin and fibroblasts. The dermis provides structural support and nutrients to the epidermis. Aging has been shown to increase cellular heterogeneity of the epidermal layer, however, it has little effect on the thickness of the epidermal layer. The supporting dermis, on the other hand, is known to thin with age and exposure to the sun and environmental contaminants. As the dermal layer provides the support and blood supply for the epidermis, the dermal layer is important in maintaining the elasticity and appearance of the skin. Disruption of the supporting dermis leads directly to sagging and consequent furrowing of the epidermis, i.e., the formation of wrinkles.

Deep wrinkles are also due to continual stretching and contraction of both the dermis and epidermis. Currently, these deep wrinkles or furrows may only be eliminated by plastic surgery or by collagen injections directly beneath the depressed areas. The fine wrinkles that occur with age and prolonged exposure to the sun and other environmental contaminants are the direct result of deterioration of the supporting dermal layer. Other environmental effects on the skin are discussed in U.S. Pat. No. 4,938,969 and U.S. Pat. No. 5,140,043, the disclosure of which is herein incorporated by reference.

As a result of the aging process and damage caused by incident radiation, a disruption of the collagen bundles that provide support to the epidermis is observed. Collagen exists normally in dense, organized patterns. During the aging process collagen becomes disorganized and less supportive of the epidermis and the dermis loses elasticity. There is a also progressive loss of circulatory support from the small blood vessels that are more numerous and close to the surface in young skin. The result of aging on skin, whether or not it has been accelerated by incident radiation, is a deterioration of the dermal layer—fewer fibroblasts, less collagen, less elastin and less circulatory support. Consequently, the normal stretching and contraction of the skin leads to damage of the dermis that is not readily corrected and wrinkling results.

Dermatologists and cosmetologists have directed their efforts to improving the appearance of skin using agents known to stimulate the growth and proliferation of epidermal cells. Newly proliferated cells provide more structure and hold more moisture, giving the skin a younger appearance. One method of causing new skin cell proliferation is accomplished by use of an irritant or chemical peel in which the uppermost layers of the epidermis are caused to slough off, leading to proliferation and replacement with new epidermal cells. While such treatment is recognized to provide some cosmetic improvement, it does not address the major causative factor—the compromised supporting dermal layer.

Considerable effort has also been expended to find ways to prevent adverse changes in the skin brought about by ultraviolet (UV) exposure. Preventative approaches include physically blocking or absorbing the UV radiation before it can enter the skin using UV absorbing compounds. This technique is effective but is cumbersome because sunblockers or absorbers must be applied before every exposure and may be washed off with water. Thus, for example, after swimming UV absorbing compounds must typically be reapplied. Further, the long-term side effects of many of the compositions containing sunblockers and/or absorbers are not known.

L-ascorbic acid has many known biological functions from enzymatic co-factor to "sparing" agent against vitamin E depletion. See, for example, Englard and Seifter, "The Biochemical Functions of Ascorbic Acid," Ann.Rev.Nutri. 6:365–406, (1986); Kunert and Tappel, "The Effect of Vitamin C on in vivo Lipid Peroxidation in Guinea Pigs as Measured by Pentane and Ethane Production, Lipids 18:271–74 (1983). The latter function may partly account for its "anti-oxidant" status. Additionally, at higher concentrations, ascorbic acid is known to react with both the superoxide and hydroxyl radicals. Superoxide and the subsequently generated hydrogen peroxide and hydroxyl radical are oxygen-containing free radicals now known to be generated in vivo under a variety of normal and pathological conditions. These radicals have been implicated as causative agents for everything from sunburn to aging and are believed to destroy lipid membranes, break down DNA, and inactivate enzymes, among other effects. An immense amount of work has been done in the last two decades documenting the deleterious behavior of oxygen radicals. Several recent texts on the subject include: *Oxy-radicals in Molecular Biology & Pathology,* D. Cerutti, 1. Fridovich, J. McCord, eds., (Alan R. Liss, Inc. New York, 1988); *Biological Role of Reactive Oxygen Species in Skin,* O. Hayaishi, S. Inamura, Y. Mayachi, eds. (Elsevier Press, New York, 1987); *Free Radicals, Aging and Degenerative Diseases,* J. E. Johnson, Jr., R. Walford, D. Harmon, J. Miguel, eds. (Alan Liss, Inc., New York, 1986); *Free Radicals in Biology and Medicine,* B. Halliwell and J. M. C. Gutteridge, eds. (Clarendon Press, Oxford, 1985); and *Oxidative Stress* Helmut Sies, ed. (Academic Press, 1985). Also addressing the subject are several symposia, including "Oxygen Radicals and Tissue Injury" Proceedings from an Upjohn Symposium (April, 1987); and "Oxygen Free Radicals," Proceedings from National Heart, Lung & Blood Institute (National Institute of Health, Washington, D.C., Dec. 1987).

As a result of the known effects of the use of ascorbic acid on damaged and aging skin, there are now various Vitamin C or ascorbic acid ointments, serums and creams that are used with varying degrees of success to prevent and/or repair damage to the skin's dermal layer. For example, it has been reported that a composition including ascorbic acid, tyrosine and a non-toxic zinc salt, preferably zinc sulfate, in a vehicle suitable for topical application, when applied to areas showing the fine wrinkles associated with aging/sun exposure, results in a readily perceivable diminution of the fine wrinkle structure. It has also been reported that ascorbic acid topical aqueous compositions are unstable unless maintained at a pH below about 3.5. This document indicated that topical compositions containing a carrier and a concentration of L-ascorbic acid above about 1% (w/v) were stable if maintained at a pH below about 3.5, and preferably below about 2.5.

It has been found, however, that currently available ascorbic acid compositions and methods fail to provide the delivery system for formulations having the desired combination of efficacy, non-irritability, stability and convenient storage solutions for topical Vitamin C applications. A significant problem of current compositions is that it is not practical to use more than 15% (w/v) ascorbic acid in a serum, cream or gel formulation for cosmetic use because the low inherent pH (circa 2–2.5) of such a formulation is often quite irritating to the skin. The break-down of the ascorbic acid in such low pH formulations due to exposure to water, heat, and air can also lead to undesirable discoloration and eventually loss of efficacy. Furthermore, if the ascorbic acid is formulated in a cream with limited water content to enhance stability of the ascorbic acid over time, changes in heat, atmospheric pressure and/or moisture content may activate the ascorbic acid, leading to unacceptable expansion and even explosion of the containers holding such creams or gels. There is accordingly a continuing need for topical ascorbic acid-based compositions that improve the efficacy and stability of such skin treatment formulations.

SUMMARY

The present invention provides stable, effective topical compositions which include ascorbic acid, generally in a relatively high pH formulation. The concentration of active ascorbic acid that is available to be delivered to the skin is maintained at a high concentration, while at the same time lowering the irritating effects commonly associated with aqueous compositions having a high concentration of organic acid. By providing, for example, a portion of the total ascorbic acid of the composition in the ascorbate salt form, the composition disclosed herein can decrease the overall irritant nature of the solution without losing efficacy or desired biological effect. The present ascorbic acid-based composition are particularly effective for topical application to reduce epidermal wrinkling, such as that resulting from intrinsic aging or photo damage. For example, applying the present compositions within about six hours to skin that has received excess sun damage can attenuate the effects due to UV exposure and decrease sunburn and cell damage. In addition, the compositions disclosed herein did not expand or lose integrity on storage. The present compositions were also far less likely to oxidize to yield an off color (e.g., to become darker or brown). Subjects using the present ascorbic acid formulations found the product to be very effective, and to yield rapid results relative to decreasing the appearance of fine lines.

The present compositions typically include up to about 50% of the total ascorbic acid present which has been prepared by dissolution in water at relatively high temperature and concentration. Ascorbic acid which has been dissolved in this manner is referred to herein as "pretreated ascorbic acid" and is prepared by dissolving a high concentration of ascorbic acid, typically at least about 20% (w/v) (i.e., at least about 200 mg/ml) in water at 60 to 90° C.

Importantly, formulations containing 50% (w/v) of the ascorbic acid content of a cream in the form of the pretreated ascorbic acid formulated as described herein do not expand, explode, or discolor due to heat, changes in atmospheric pressure, or improper storage, all of which have proved to be problems in manufacturing, storing and distributing formulations of pure L-ascorbic acid and its direct break down products.

Embodiments of the present compositions commonly include water, at least about 5.0% (w/v) ascorbic acid, and have a pH of more than 3.5. Preferably, the compositions have a pH of about 3.6 to about 4.2, and, more preferably, about 3.7 to 4.0. The compositions typically also include (a) non-toxic zinc salt and/or (b) a stimulant of protein synthesis and/or precursor to melanin synthesis (e.g., a tyrosine compound). The compositions may also include an anti-inflammatory compound, such as an aminosugar and/or a sulfur-containing anti-inflammatory compound. The topical compositions may be in any of a number of common forms, such as an aqueous solution ("a serum"), a hydrophilic lotion-, an ointment-, a cream, or a gel. Typically, the topical composition includes a pharmaceutically acceptable carrier and may also include one or more other formulation additives, such as surfactant(s), thickener(s), other antioxidants and/or fragrance.

The "high pH" formulations of the present compositions are less irritating than high concentrations of L-ascorbic acid (with its inherent low pH, e.g., circa 2–2.5) because the relatively higher pH avoids the skin irritation problem often encountered with harsh chemical peels or solutions with pH values below 3.5. The present compositions were also found to be very stable on short and long term storage, while maintaining a high degree of effectiveness.

The present invention also includes a method of treating damage to skin, such as often arises due ultraviolet light exposure and/or aging. The method includes applying the present topical composition to a damaged portion of the skin, For example, the present composition is typically applied topically to the locus of wrinkles.

BRIEF DESCRIPTION OF THE DRAWINGS

The invention will become more fully understood from the following detailed description, taken in conjunction with the accompanying drawings, in which.

DETAILED DESCRIPTION

Figure 1:
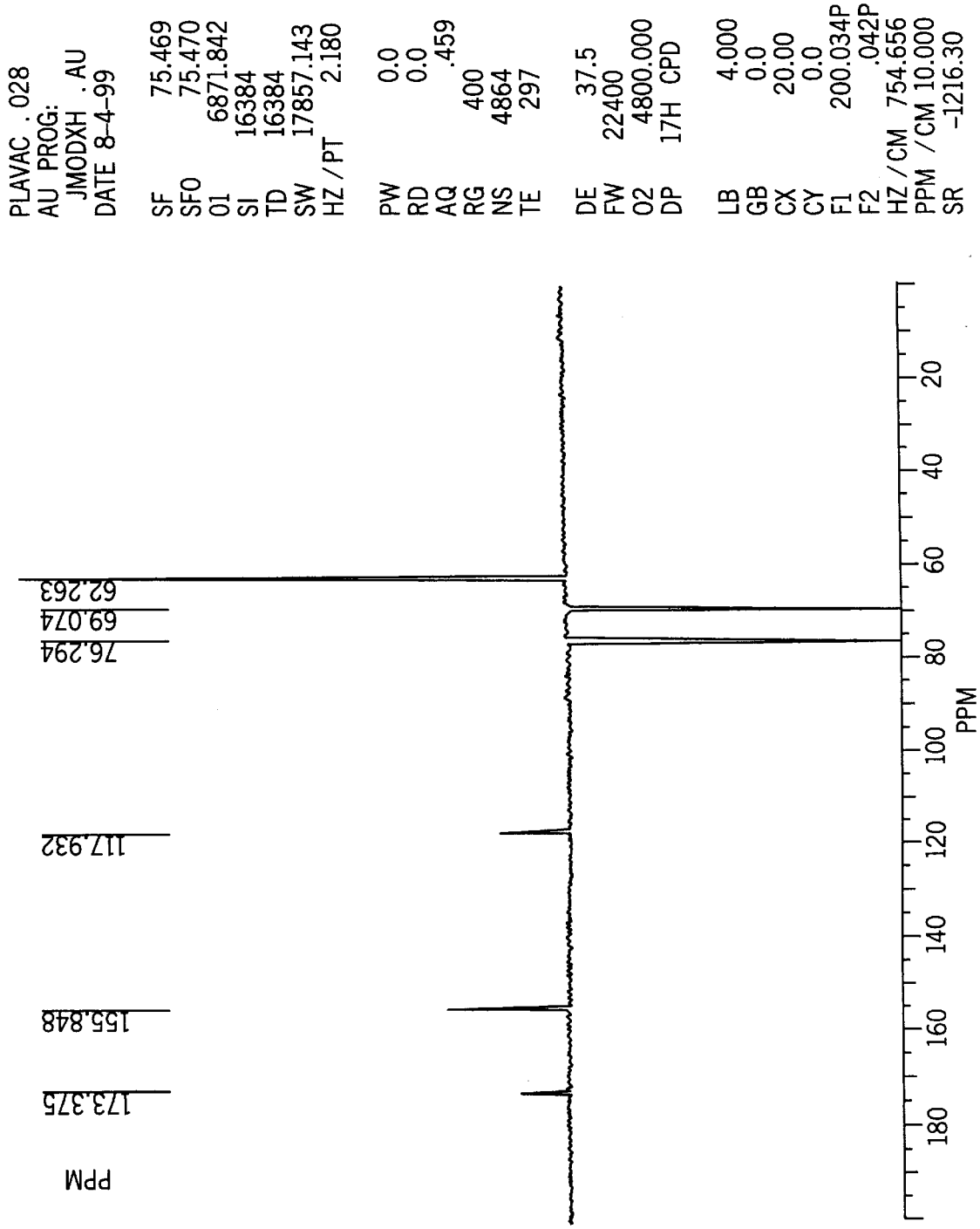
FIG. 1 shows a C13 NMR of a 10% (w/v) solution of "native" ascorbic acid after storage for one week at 37° C.

Long shelf-life and extended stability (e.g., for at least two years) is normally required for any cosmetic product to be distributed through ordinary channels in which there must be stored inventory to meet market demand without the concern that the inventory will deteriorate before being sold. The present ascorbic acid-based compositions have good efficacy and storage stability, and low skin irritability. These topical ascorbic acid based compositions are particularly effective for reducing epidermal wrinkling resulting from intrinsic aging or photo damage. The compositions may also be used prophylactically to ameliorate the photo-induced damage which can result from exposure of skin to sunlight and other harmful irradiation.

The compositions typically include at least about 5.0% (w/v) ascorbic acid. Herein, the amount of ascorbic acid present in a composition refers to the total amount of ascorbic acid and ascorbate present stated as if all was present in the acid form. In other words, a solution which includes 0.5 mole ascorbic acid and 0.5 mole of an ascorbate salt contains the same total amount of ascorbic acid as a solutions which include either 1.0 mole ascorbic acid or 1.0 mole of an ascorbate salt.

While the present compositions commonly include at least about 5.0% (w/v) total ascorbic acid, it is generally advantageous to include higher concentrations, typically at least about 10% (w/v) and often concentrations in the range of about 15 to about 25% (w/v) ascorbic acid. Because of the potential problems of skin irritation with formulations containing high concentrations of ascorbic acid, it is generally advantageous to adjust the pH of such formulations to at least about 3.5. To achieve an optimum combination of low irritability and high stability, the present compositions are typically formulated to have a pH of about 3.7 to about 4.1 and, preferably, about 3.8 to about 4.0.

It has found that ascorbic acid-based topical formulations in which a substantial portion of the ascorbic acid has been "pretreated" exhibit particularly good storage stability. As noted above, for the purposes of this application, pretreated ascorbic acid refers to ascorbic acid which has been dissolved in water at a relatively high temperature to form a concentrated ascorbic acid solution. Typically, the ascorbic acid is dissolved in water at about 60 to about 90° C. (preferably about 75 to about 80° C.) to form a concentrated solution which contains at least about 20% (w/v) ascorbic acid. During this pretreatment, the ascorbic acid is dissolved in the acid form, i.e., the resulting solution will have a relatively low pH (circa 2.0–2.5). After dissolution, the concentrate is generally heated for an additional period of time (e.g., 0.25 to 1.0 hour) and cooled to below about 40° C. before being incorporated into the final formulation. If the pretreated concentrate is to be stored prior to formulation, it is preferably stored at room temperature or below (e.g., about 3 to about 20° C.) and/or under conditions which exclude oxygen-containing gases such as air (e.g., in a sealed container or blanketed with an inert gas such as argon or nitrogen). In the present compositions, commonly at least about 10% of the ascorbic acid present has been pretreated. Typically, no more than about 50% of the ascorbic acid present has been pretreated. This allows the enhanced stability properties to be obtained while minimizing the additional processing steps and cost associated with the pretreatment of the ascorbic acid.

Figure 2:
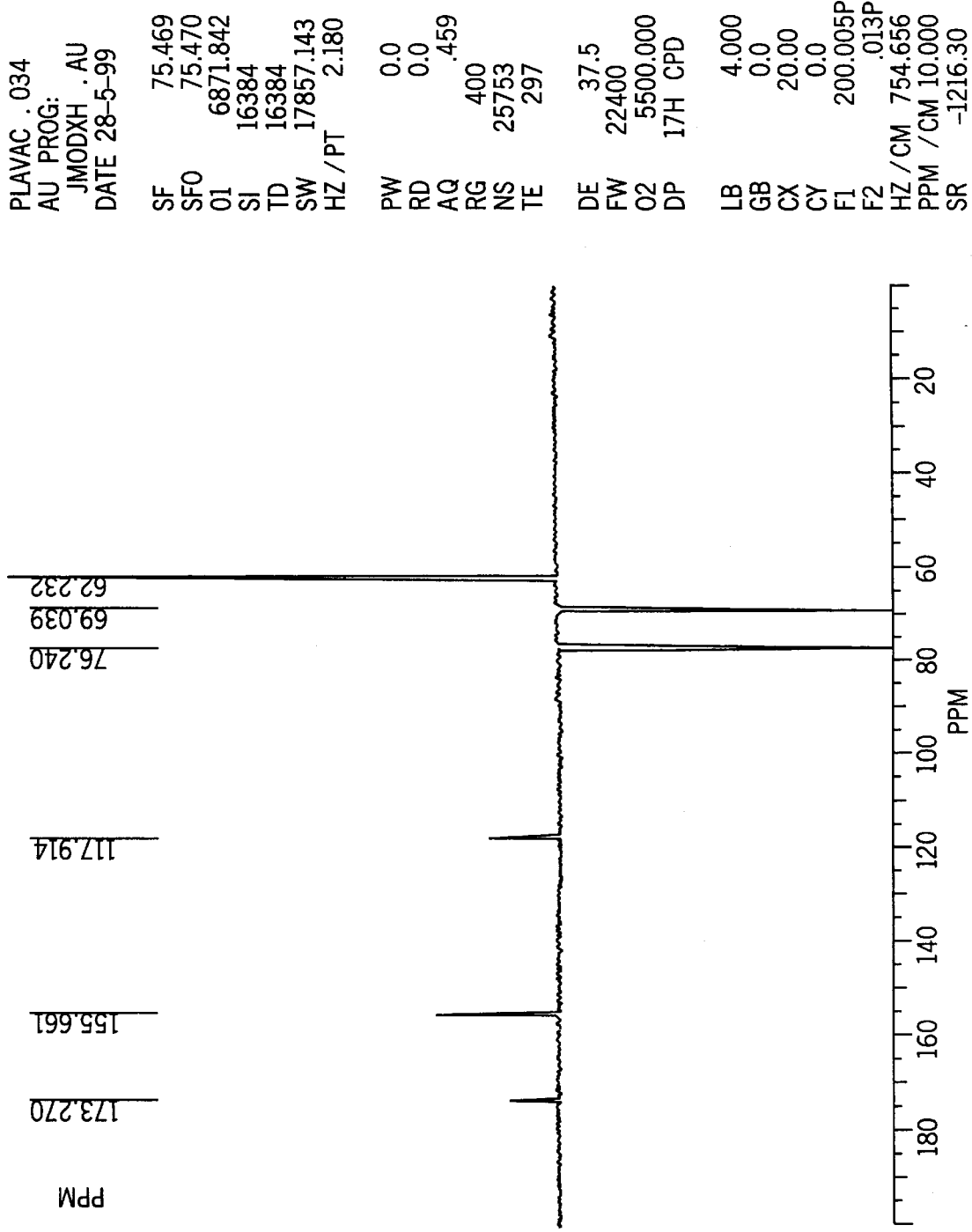
FIG. 2 shows a C13 NMR of a 1:1 mixture of a 10% (w/v) solution of "native" ascorbic acid and a 30% (w/v) solution of "pretreated" ascorbic acid after storage of the mixture (at pH 2.3) for one month at room temperature.
Figure 3:
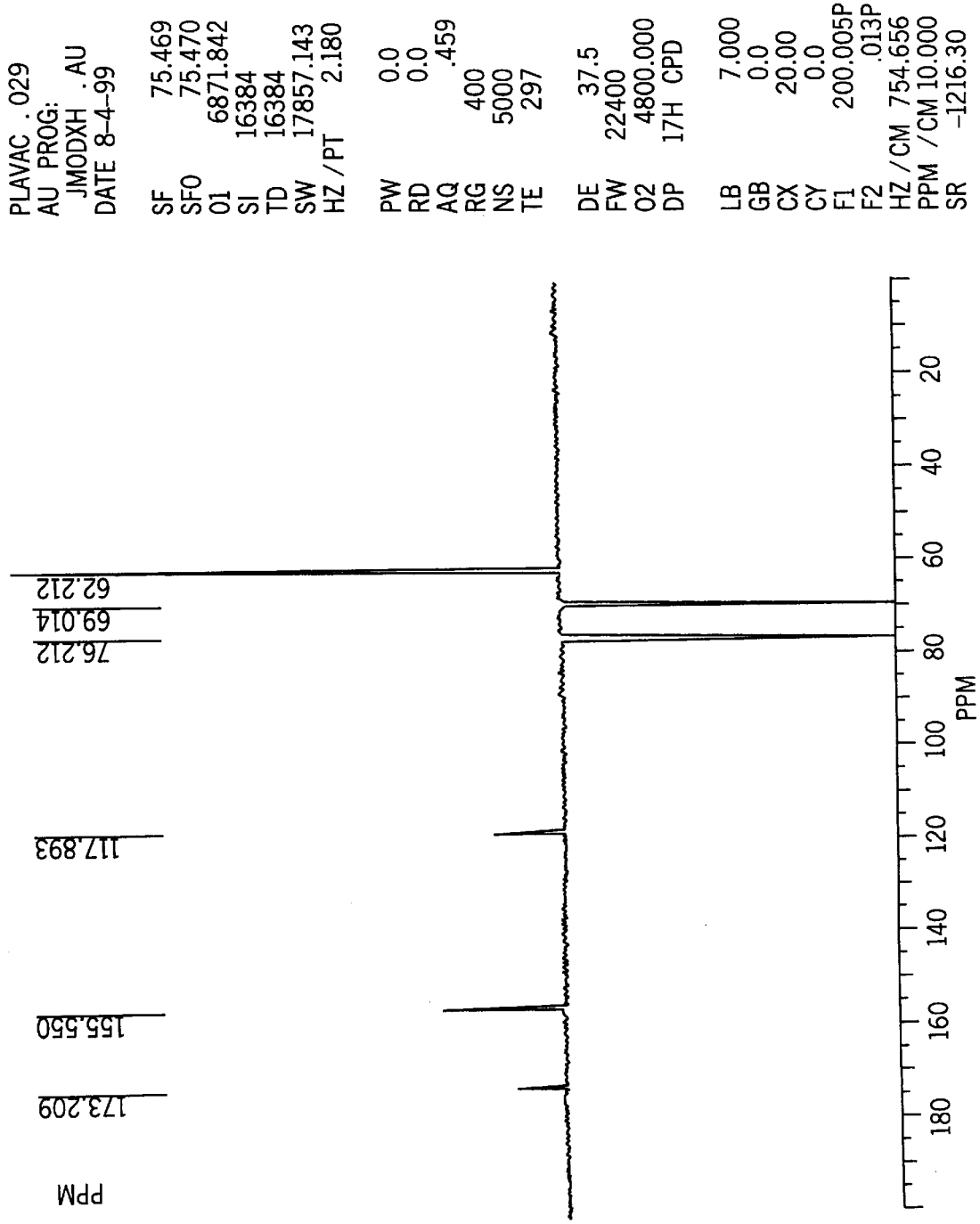
FIG. 3 shows a C13 NMR of a 30% (w/v) solution of "pretreated" ascorbic acid after storage for one week at 37° C.

To test and quantitate the stability of composition containing "pretreated" ascorbic acid, nuclear magnetic resonance (NMR) spectra of stored samples of the following ascorbic acid-based solutions: (i) a 10% (w/v) solution of "native" ascorbic acid; (ii) a 1:1 mixture of the 10% (w/v) solution of "native" ascorbic acid and a 30% (w/v) solution of "pretreated" ascorbic acid; and (ii) the 30% (w/v) solution of "pretreated" ascorbic acid after storage. The results, shown in FIGS. 1, 2 and 3 respectively, demonstrate the stability of the solutions under storage conditions. Somewhat accelerated storage testing is often carried out by storing solutions at 37° C. The results of tests (see, e.g., FIGS. 1 and 3) demonstrated that both a 10% (w/v) solution of "native" ascorbic acid and a 30% (w/v) solution of "pretreated" ascorbic acid were stable after storage at 37° C. for one week.

As an example, containers having a 1 to 20% (w/v) concentration of a mixture of pretreated ascorbic acid in a 1:1 to 1:10 ratio, together with ascorbic acid formulated under more standard conditions (i.e., dissolved or added in solid form to a formulation at temperatures of about 20 to about 40° C.—"native ascorbic acid") were quite stable when shipped and/or stored under adverse conditions, or even when heated. The stability of such formulations was enhanced in comparison to conventional low pH formulations containing untreated ascorbic acid, e.g., low pH creams containing 10% (w/v) untreated ascorbic acid.

The present compositions generally also include a nontoxic zinc salt. The zinc salt is preferably a water soluble zinc salt such as zinc sulfate. The zinc salt is generally present in about 0.5 to about 5.0% (w/v). Very effective results can typically be obtained with compositions which include no more than about 3.0% (w/v) zinc salt. For example, a number of present compositions are commonly formulated with about 0.5 to about 2.0% (w/v) zinc sulfate together with the other components described herein.

The composition of the present invention may further include one or more compounds capable of serving as a stimulant of protein synthesis and/or precursor to melanin synthesis. This component is generally present in about 1 to about 10% (w/v), and more preferably 3 to about 8% (w/v), based on the total composition. Typically, this component includes a tyrosine compound. As employed herein, a "tyrosine compound" is tyrosine or a compound which is capable of generating tyrosine upon chemical and/or biological transformation. Examples of suitable tyrosine compounds for use in the present compositions include tyrosine, N-acetyl-tyrosine, tyrosine ethyl ester hydrochloride, and tyrosine phosphate.

The present compositions may also include a compound which can function as an anti-inflammatory agent. Examples of suitable anti-inflammatory agents include anti-inflammatory sulfur-containing compounds and anti-inflammatory aminosugars. The sulfur-containing anti-inflammatory compound is typically a sulfur containing amino acid or related derivative such as cystine, cysteine, N-acetyl cysteine, glutathione, cysteamine, S-methylcysteine, methionine and the like. Examples of suitable anti-inflammatory aminosugars include glucosamine, mannosamine, N-acetylmannosamine, galactosamine, glucosamine-6-phosphate, N-acetylglucosamine, N-acetylmannosamine, N-acetylgalactosamine and the like. For example, by adding D-glucosamine hydrochloride to the present compositions (in circa 5–20% (w/v)), cellular damage due to excess sun exposure can be minimized even if applied roughly 12 hours after exposure due to the anti-inflammatory effects of glucosamine in concert with ascorbic acid.

The ascorbic acid and tyrosine compound components of the present compositions may be formulated in part or whole in a neutralized or salt form. Acceptable amine salts include the acid addition salts (e.g., formed with a free amino group of a tyrosine compound) and may be formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, histidine, procaine and the like. As noted elsewhere herein, since the present compositions have a pH of 3.5 or above (and typically at least about 3.7) the ascorbic acid is typically at least partially present in the form of ascorbate salt(s). Commonly, the pH of the composition is adjusted to the desired value by adding sufficient base, such as sodium hydroxide, potassium hydroxide and/or ammonium hydroxide, to achieve the desired value. In such situations, the ascorbate would exist at least in part in the form of sodium hydroxide, potassium and/or ammonium ascorbate.

The water used for preparing the compositions of the present invention may be distilled and/or deionized, but any water may be used that does not contain contaminants which would affect the stability of the ascorbic acid present in the composition. For example, the presence of certain metal ions such as copper and iron salts, is known to effect the stability of ascorbic acid. The effects of water of varying purity on ascorbic acid stability is discussed in Meucci, et al., "Ascorbic Acid Stability in Aqueous Solutions," Acta Vitaminol. Enzymol. 7(34): 147–54 (1985), the disclosure of which is incorporated herein by reference.

The present compositions typically also include a pharmaceutically acceptable carrier. Carriers for topical application useful in practicing the invention include, but are not limited to, alkyleneglycols, or alkyleneglycols in combination with one or more derivatives of hydroxyalkylcellulose. In one illustrative embodiment, the alkylene glycol is propyleneglycol and the hydroxyalkylcellulose is hydroxypropylcellulose. When a combination of alkyleneglycol and hydroxyalkylcellulose is used, a useful ratio of alkyleneglycol to hydroxyalkylcellulose is from about 30:1 to 5:1. Without limitation, other carriers known to those skilled in the art that are compatible with water and are biologically acceptable are expected to provide equivalent compositions within the scope of this invention. For example, alcohols such as ethanol and propanol, glycols such as butylene or hexylene glycol, and polyols such as sorbitol or glycerol may be suitably employed. Other examples of suitable carriers include polyethylene or polypropylene glycols. Also contemplated as carriers for use in the present compositions are biologically acceptable hydroxyalkylcelluloses.

The phrase "pharmaceutically acceptable" refers to molecular entities and compositions that do not produce an allergic or similar untoward reaction when administered to a human. The pharmaceutically acceptable carriers and additives employed in the present compositions are compatible with at least one formulation of the ascorbic acid/ascorbate mixture, tyrosine compound and zinc salt containing compositions as described herein.

Amino acids employed in the present compositions will generally be in the left-handed chiral form of the amino acid (i.e., L-amino acid(s)). The amino acids should be as pyrogen free as possible and should meet sterility, pyrogenicity, general safety and purity standards as required by FDA Office of Drug standards. The amino acids may even act as buffers for the present solutions or may even be used to adjust the pH of the solution to above 3.5. Illustrative examples of the present compositions can be produced as follows. The appropriate amounts of the acid forms of native and untreated ascorbic acid are mixed and/or dissolved in water. A water soluble, non-toxic zinc salt is then added and the mixture is mixed (via stirring or agitation) until the zinc salt has dissolved. Other components, such a tyrosine compound and/or anti-inflammatory compound(s) are then added if desired. After the other ingredients have been added to the solution, the pH is adjusted by adding an appropriate amount of a base such as sodium hydroxide or sodium carbonate to produce a pH of about 3.8 to about 4.0. The resulting solution can be employed as a topical composition in this form (i.e., a "serum") or may be used to produce any of a variety of conventional formulations well known to those skilled in the art, e.g., as a cream, lotion or gel.

The present topical composition may be in the form of an aqueous solution (i.e., "serum") or blended into a tissue compatible vehicle, such as hydrophilic lotion-, ointment-, cream- or gel-based vehicle. Such vehicles are well known in the art and commercially available for formulation of active ingredients into a suitable form for topical application. Exemplary of such vehicles are the commercially available Dermabase and Unibase formulations.

The present composition can include one or more of a variety of optional ingredients, such as coloring agents, opacifying agents and the like. The formulation can include, in addition to the components described hereinabove, other active ingredients, such as antibiotics, analgesics, anti-allergenics and the like. The formulation is commonly applied to the skin as a lotion or cream to be rubbed on body tissue over the desired area. For optimum efficacy treatment in accordance with the presented method should be initiated as early as possible following exposure to sunlight or another radiation source. The formulation is generally applied to the skin once or twice daily. As noted elsewhere herein, the present composition may also be used to inhibit the effects of aging and/or photo damage on the skin.

Administration

Upon formulation, solutions will be administered in a manner compatible with the dosage formulation and in such amount as is therapeutically effective. The formulations are easily administered in a variety of dosage forms such as direct topical application, application via a transdermal patch and the like.

For topical administration in an aqueous solution, for example, the ascorbic acid/ascorbate mixture, tyrosine compound and zinc salt containing compositions may be used directly on the skin without any toxic effects to the animal or patient. Alternatively, the ascorbic acid/ascorbate mixture, tyrosine compound and zinc salt containing compositions identified herein, may be dissolved or resuspended in a suitable buffer prior to mixing, if necessary. Liquid diluents may first be rendered isotonic with sufficient saline or glucose solutions.

The present aqueous solutions are especially suitable for topical administration. As discussed above, however, other ascorbic acid-based formulations may also be used quite effectively. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

While the making and using of various embodiments of the present invention are discussed in detail below, it should be appreciated that the present invention provides many applicable inventive concepts which can be embodied in a wide variety of specific contexts. The specific embodiments discussed herein are merely illustrative of specific ways to make and use the invention and do not delimit the scope of the invention. Various modifications and combinations of the illustrative embodiments, as well as other embodiments of the invention, will be apparent to persons skilled in the art upon reference to the description.

What is claimed is:

1. A topical composition comprising:
    at least about 5.0% (w/v) ascorbic acid;
    water;
    nontoxic zinc salt; and
    tyrosine compound;
    wherein the composition bas a pH which is adjusted to about 3.6 to about 4.2 by adding a sufficient amount of base; and at least about 10 wt. % of the total ascorbic acid is pretreated ascorbic acid, and the pretreated ascorbic acid is produced by dissolving at least about 20% (w/v) ascorbic acid in water at 60 to 90° C.

2. The composition of claim 1 wherein the composition has a pH of about 3.7 to about 4.0.

3. The composition of claim 1 further comprising an anti-inflammatory compound.

4. The composition of claim 3 wherein the anti-inflammatory compound includes sulfur-containing anti-inflammatory compound.

5. The composition of claim 4 wherein the sulfur-containing anti-inflammatory compound is selected from the group consisting of cystine, cysteine, N-acetyl cysteine, glutathione, cysteamine, S-methylcysteine, methionine and mixtures thereof.

6. The composition of claim 3 wherein the anti-inflammatory compound includes aminosugar.

7. The composition of claim 6 wherein the aminosugar includes glucosamine, mannosamine, galactosamine, glucosamine-6-phosphate, N-acetylglucosamine, N-acetylmannosamine, N-acetylgalactosamine and mixtures thereof.

8. The composition of claim 1 wherein the ascorbic acid is present in an amount of about 15% (w/v) to about 25% (w/v).

9. The composition of claim 1 wherein the water is selected from the group consisting of distilled water, deionized water, distilled deionized water and mixtures thereof.

10. The composition of claim 1 wherein the non-toxic zinc salt is present in an amount of about 0.5 to about 5% (w/v).

11. The composition of claim 1 wherein the non-toxic zinc salt is zinc sulfate.

12. The composition of claim 1 wherein the tyrosine compound is selected from the group consisting of tyrosine, N-acetyl-tyrosine, tyrosine ethyl ester hydrochloride, tyrosine phosphate and mixtures thereof.

13. The composition of claim 1 wherein the tyrosine compound is present in an amount of about 1 to about 10% (w/v).

14. The composition of claim 1 further comprising a pharmaceutically acceptable carrier.

15. The composition of claim 14 wherein the pharmaceutically acceptable carrier includes glycerol, propyleneglycol, sorbitol, hydroxypropylcellulose or a mixture thereof.

16. The composition of claim 14 wherein the pharmaceutically acceptable carrier includes alkyleneglycol, hydroxyalkylcellulose or a mixture thereof.

17. A topical composition comprising:
    an aqueous solution comprising at least about 5% (w/v) ascorbic acid, wherein at least about 10 wt. % of the total ascorbic acid is pretreated ascorbic acid, and the pretreated ascorbic acid is produced by dissolving at least about 20% (w/v) ascorbic acid in water at 60 to 90° C.;
    tyrosine compound; and
    non-toxic zinc salt;
    wherein the composition has a pH which is adjusted to about 3.6 to about 4.2 by adding a sufficient amount of base.

18. The composition of claim 17 wherein the ascorbic acid is present in an amount of about 15 to about 25% (w/v) and said composition a pH of about 3.7 to about 4.0.

19. The composition of claim 17 wherein the tyrosine compound is present in an amount of about 1 to about 10% (w/v) and the non-toxic zinc salt is present in an amount of about 0.5 to about 5% (w/v).

20. The composition of claim 17 further comprising an anti-inflammatory compound which includes sulfur-containing anti-inflammatory compound, aminosugar or a mixture thereof.

21. A topical composition comprising:
    an aqueous solution comprising at least about 5.0% (w/v) ascorbic acid, wherein about 10 to about 50 wt. % of the total ascorbic acid is pretreated ascorbic acid, and the pretreated ascorbic acid is prepared by dissolving at least about 20% (w/v) ascorbic acid in water at 60 to 90° C.;
    tyrosine compound; and
    non-toxic zinc salt;
    wherein the composition has a pH which is adjusted to about 3.6 to about 4.2 by adding a sufficient amount of base.

22. The composition of claim 21 wherein the aqueous solution has a pH of about 3.7 to about 4.0.

23. The composition of claim 21 wherein the non-toxic zinc salt is present in an amount of about 0.5 to about 5% (w/v).

24. The composition of claim 21 wherein the tyrosine compound is present in an amount of about 1.0 to about 10% (w/v).

25. The composition of claim 21 further comprising a precursor of melanin synthesis other than said tyrosine compound.

26. The composition of claim 21 wherein the ascorbic acid is present in an amount of about 15 to about 25% (w/v).

27. A method of treating damage to skin comprising applying a topical composition to the skin, wherein the topical composition comprises:
    at least about 5.0% (w/v) ascorbic acid;
    water;
    non-toxic zinc salt; and
    tyrosine compound;
    wherein the composition has a pH which is adjusted to about 3.6 to about 4.2 by adding a sufficient amount of base; and at least about 10 wt. % of the total ascorbic acid is pretreated ascorbic acid, and the pretreated ascorbic acid is produced by dissolving at least about 20% (w/v) ascorbic acid in water at 60 to 90° C.

28. The method of claim 27 wherein the topical composition is applied to the skin once or twice daily.

29. The method of claim 27 wherein the topical composition is an aqueous solution, a lotion, an ointment, a cream, or a gel.

30. A method of treating damage to skin comprising applying a topical composition to the skin the topical composition comprising
    an aqueous solution including at least about 5.0% (w/v) ascorbic acid, wherein about 10 to about 50 wt. % of the total ascorbic acid is pretreated ascorbic acid, and the pretreated ascorbic acid is prepared by dissolving at least about 20% (w/v) ascorbic acid in water at 60 to 90° C.;
    tyrosine compound; and
    non-toxic zinc salt;
    wherein the composition has a pH which is adjusted to about 3.6 to about 4.2 by adding a sufficient amount of base.

31. The method of claim 30 wherein the non-toxic zinc salt is present in an amount of about 0.5 to about 5% (w/v) and the tyrosine compound is present in an amount of about 1.0 to about 10% (w/v).

32. A method of protecting skin against damage due to exposure to radiation or chemicals comprising applying a topical composition to the skin, wherein the topical composition comprises:
    at least about 5.0% (w/v) ascorbic acid;
    water;
    non-toxic zinc salt; and
    tyrosine compound;

wherein the composition has a pH which is adjusted to about 3.6 to about 4.2 by adding a sufficient amount of base; and at least about 10 wt. % of the total ascorbic acid is pretreated ascorbic acid, and the pretreated ascorbic acid is produced by dissolving at least about 20% (w/v) ascorbic acid in water at 60 to 90° C.

33. A method of protecting skin against damage due to exposure to radiation or chemicals comprising applying a topical composition to the skin, the topical composition comprising non-toxic zinc salt; tyrosine compound; and an aqueous solution including at least about 5.0% (w/v) ascorbic acid, wherein about 10 to about 50 wt. % of the total ascorbic acid is pretreated ascorbic acid, and the pretreated ascorbic acid is prepared by dissolving at least about 20% (w/v) ascorbic acid in water at 60 to 90° C. and the composition has a pH which is adjusted to about 3.6 to about 4.2 by adding a sufficient amount of base.

34. The method of claim 33 wherein the radiation includes ultraviolet radiation.

35. The method of claim 33 wherein the non-toxic zinc salt is present in an amount of about 0.5 to about 5% (w/v) and the tyrosine compound is present in an amount of about 1.0 to about 10% (w/v).

\* \* \* \* \*